United States Patent [19]

Holupko

[11] 4,421,414

[45] Dec. 20, 1983

[54] HIGH EFFICIENCY MIXING METHOD

[75] Inventor: Darrell Holupko, Fairport, N.Y.

[73] Assignee: General Signal Corporation, Stamford, Conn.

[21] Appl. No.: 336,120

[22] Filed: Dec. 31, 1981

Related U.S. Application Data

[63] Continuation of Ser. No. 134,019, Mar. 5, 1980, abandoned.

[51] Int. Cl.³ .............................................. B01F 7/16
[52] U.S. Cl. ................................ 366/348; 241/46.17; 261/93
[58] Field of Search ........ 366/102, 243, 247, 262–265, 366/276–279, 281–283, 317, 330, 65, 326, 348; 261/87, 93; 416/184, 199; 241/46.17, 189 A

[56] References Cited

U.S. PATENT DOCUMENTS 3,387,832  6/1968  Nelson ................................. 261/93
3,512,762  5/1970  Umbricht ....................... 366/102 X Primary Examiner—Philip R. Coe
Attorney, Agent, or Firm—Jeffrey S. Mednick; Harold S. Wynn

[57] ABSTRACT

The high efficiency mixing method uses an impeller with a central axial hub adapted for attachment to a rotatable driven shaft of a mixer motor. Under certain operating conditions, the method has a higher mass transfer efficiency, in both directions of rotation when compared to other methods using other impellers.

1 Claim, 5 Drawing Figures

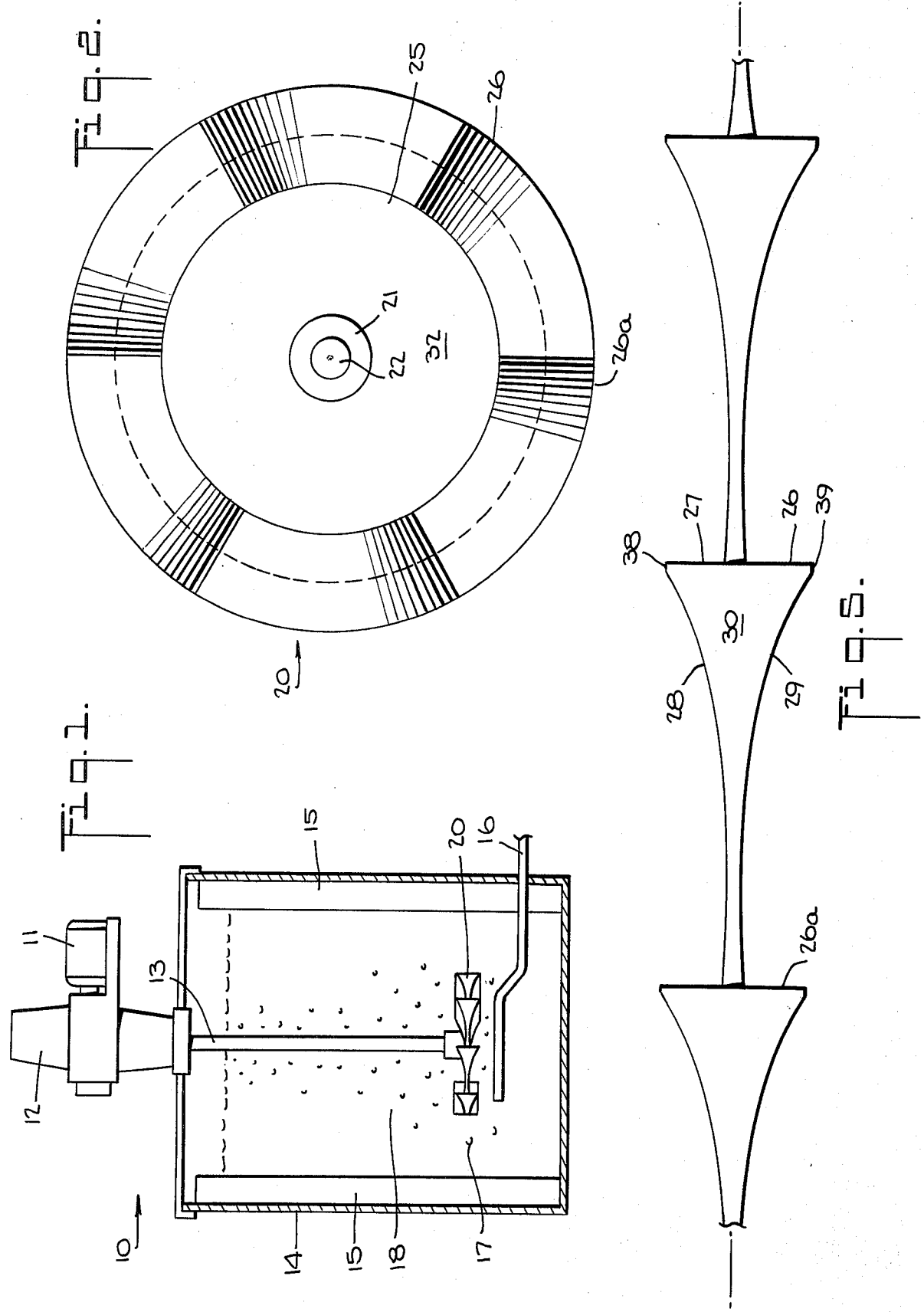

HIGH EFFICIENCY MIXING METHOD

This application is a continuation of application Ser. No. 06/134,019, filed Mar. 5, 1980, and now abandoned.

BACKGROUND

This invention relates to a mixing apparatus and method in general, and, in particular, to a mixing impeller with the blades having two different surface configurations and a method using such an apparatus.

In many areas of technology, it is frequently desirable to mix a fluid with one or more other substances. It has been necessary to mix gasses, liquids, and solids, of a powdered or particulate nature, together with a liquid contained in a tank. The mixing process and mixer performance involve the interrelation of three known factors: an impeller, a fluid, and a mixing vessel which may include baffles that contain the fluid. The impeller is used to move and agitate the fluid, and mixing results from this fluid motion.

Impellers may be divided into two general classifications, axial and radial flow, depending upon their shape, positioning, and vessel geometry. The flow pattern developed by a mixer will depend upon the geometric configuration of the impeller and the physical properties of the fluid mixture. For examples of various shaped impellers, including a propeller, an arrowhead impeller, and a flat blade impeller, see U.S. Pat. Nos. 2,165,916; 2,384,952; and 2,637,538, respectively.

In a gas-liquid mixing operation, the principal function of the impeller is to disperse a gas stream to an effective bubble size and interfacial area. At the same time, the impeller should increase the turbulence in the liquid and provide as uniform as possible distribution of the gas within the liquid. The flat blade turbine have proven to be particularly useful in achieving the desired gas-liquid mixing.

The flat blade turbine impeller has a disc which is open on both sides in order to assure good contact for any gas both above and below the turbine level. Hence, it provides good suction above the hub of the disc to draw bubbles downward to the impeller and prevents short-circuiting of gas from below the impeller upward along the impeller shaft. Accordingly, the flat blade turbine imparts both an axial flow and a radial flow, thereby maximizing the turbulence of the liquid with which the gas is mixed.

The blades of such a turbine are spaced radially from the hub since it has been found by experiment that little fluid motion takes place adjacent to the hub of the impeller. In addition, its blades are not shrouded (covered) thereby further contributing to their ability to create turbulence as the fluid is subjected to both axial and radial forces generated by the turbine. Such characteristics of impeller design (radial spaced blades, uncovered, and unshrouded blades), served to distinguish mixing impellers from impellers used in other types of devices, such as pumps.

In pumps, where turbulence is undesirable, it is a common practice to provide flow in only one direction (axial or radial). Usually only one surface of a disc carries blades, and the blades of the pump impeller normally extend from a central hub to the end of the disc in order to separate and seal a plurality of pump chambers. For an example of one such type of pumping impeller, see U.S. Pat. No. 3,136,254. Because of their marked differences in purpose and function, pump impellers are not generally considered to be useful for mixing operations and vice versa.

During some mixing operations, it is often desirable to vary the power input to a mixer motor if the physical properties of the mixture change, e.g. the mixture's viscosity increases. Then the load on the motor may increase, and the motor speed will have to be adjusted in order to prevent an overload. In other operations it is desirable to operate the mixing process at a different rate. For example, in a fermentation cycle, oxygen is supplied to propagate microorganisms. At the beginning of such a cycle, the population is minimal and the oxygen demand is low. Hence, a relatively low gas rate and a low mixer speed (low horsepower) is sufficient during the start of such a cycle. However, a higher gas rate and higher mixer speed is needed as the population grows.

In such operations, it has in the past been necessary to provide a variable speed control for the motor or a special two-speed motor and appropriate switchgear in order to accomplish the aforementioned desired result. Such variable speed controls and special motors are expensive. Accordingly, it would be desirable to have an inexpensive means for altering the power required to turn an impeller in a mixing apparatus without adjusting the speed of the motor.

In other mixing operations, especially related to mass transfer, such as the fermentation cycle, the efficiency of the mixing impeller is a function of mass transferred per unit power consumed. Accordingly, it would be desirable to provide a more energy efficient impeller for mass transfer operations.

An object of the present invention is to provide an improved process for agitating liquids which substantially obviates one or more of the limitations and disadvantages of the described prior art systems.

Another object of the present invention is to agitate liquids with an impeller having blades adapted to introduce flow at different power numbers when rotated at the same speed in respective forward and reverse directions.

Another object of the present invention is to provide an improved process permitting operation of an agitator at a constant speed without overload under variable load conditions by selectively governing the direction of rotation.

Other objects, purposes, and characteristic features of the present invention will be in part obvious from the accompanying drawings, and in part pointed out as the description of the invention progresses.

SUMMARY OF THE INVENTION

The invention is a process for agitating liquids having different viscosities by an impeller driven at substantially the same given speed for either direction of rotation comprising the steps of agitating a liquid of relatively light viscosity by rotating the impeller in a given direction at the given speed, the impeller having a plurality of blades substantially longer than they are wide disposed in end-to-end relationship about the periphery of a disc of the impeller, the blades having first longitudinal arcuate flow inducing surfaces for inducing flow primarily when the impeller is rotated in the given direction, and second, flat end, flow inducing surfaces for inducing flow primarily when the impeller is rotated in the opposite direction.

A substance is introduced into the liquid whereby the viscosity of the liquid is increased.

The direction of rotation of the agitator is reversed upon increase in the viscosity of the liquid to render the second, flat end, flow inducing surfaces primarily effective to induce flow, rather than the first longitudinal arcuate flow inducing surfaces to reduce load on the impeller when rotated at the same given speed in the opposite direction.

This results in the load on the impeller being reduced upon increase in the viscosity of the liquid upon changing the direction of rotation of the impeller, without requiring reduction in the speed of rotation of the impeller.

In other words it is a feature of the invention that the impeller, when rotated in one direction at a given speed, in a given fluid, draws considerably less power than when rotated in the opposite direction at the same speed in the same fluid. The inventive impeller has two embodiments, one in which the blade-sections are open and the other in which the blade-sections are closed. Both of these embodiments have the same dual power draw characteristic, although the absolute power numbers of the two impellers (when compared on the same basis) are different. Accordingly, if the motor driving the impeller begins to overload due to a change in fluid properties or operating characteristics, the direction of rotation can be changed in order to decrease the power drawn by the impeller and thereby compensate for the change in the fluid properties.

Prior to developing the invention, it was known that some impellers having arcuately-shaped blades drew two different levels of power when rotated in opposite directions at the same speed. Although this difference in the power drawn was measurable, it was insignificant with respect to the power differential required for most mixing operations. Hence, it was an unexpected result that the power numbers for the invention differ by more than 65%. In addition, it might be expected that the power draw would be larger when the impeller was rotated in a direction to present the flat surface as the leading surface. However, as a further result, exactly the opposite occurred. Hence, it is the more streamlined, arrowhead-like surface which draws more power when the impeller is rotated in the direction in which the arrowhead points.

It is another feature of the invention that the power drawn for a particular mass transfer requirement is less than the power drawn by flat blade turbines that are typically used in mass transfer operations.

Still another feature is a novel mass transfer method that exhibits a relatively high efficiency for low horsepower inputs.

Having thus summarized the invention, those skilled in the art are directed to the accompanying drawings and the following detailed specification.

DRAWINGS

FIG. 1 is a schematic, elevational view of the invention in a mixing vessel.

FIG. 2 is a plan view of the invention.

FIG. 5 is a developed view of the invention.

DETAILED DESCRIPTION

Figure 3:
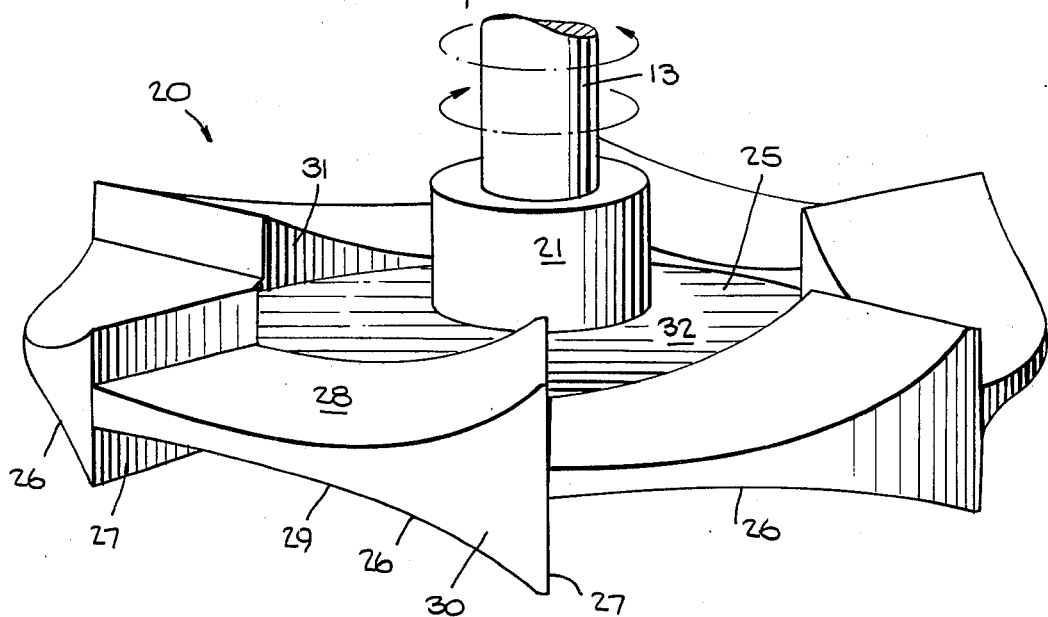
FIG. 3 is a perspective edge view of the invention with the blades closed on their sides.

Prior to discussing the invention as shown in the accompanying drawings, it is deemed helpful to the reader to define certain terms which shall be used throughout the remainder of the specification. To this end, the term "power number" (Np) is defined as a nondimensional constant which indicates the relative amount of power needed to drive turbines of different geometric configurations under identical operating conditions. The term "dual power number impeller" is defined as an impeller in which the power number in one direction of rotation is different from the power number in the reverse direction of rotation. The power number ratio (Npx/Npy) is defined as ratio of the lower power number to the higher power number when comparing power numbers measured in both rotational directions. Therefore, the power number ratio is always equal to or less than one.

Referring to the drawings, in particular, FIG. 1, there is generally shown at 10 a mixing apparatus. Included is a motor 11 for operating a drive 12 which is adapted to turn a rotatable shaft 13. The motor 11 and drive 12 are suitably suspended above a tank 14 for containing a liquid 18. Baffles 15 are suitably provided along the inner surface of tank 14 in a manner well known in the art. A sparging pipe 16 passes through the tank 14 for introducing a gas 17 into the liquid 18. The dual power number impeller 20 of the invention is fixedly mounted to the end of rotatable shaft 13. In a manner well known in the art, the sparging pipe 16 is adapted to discharge the gas 17 underneath the impeller 20.

With reference to FIGS. 2, 3, and 5, the dual power number impeller 20 is shown having an axial hub 21 with an axial opening 22 to accommodate the rotatable shaft 13. The hub 21 is fixed to the shaft by any suitable means. Mounted on hub 21 is a circular disc 15 having an upper face 32 and a lower face 33. As shown, the disc 25 is open to the liquid on both of its faces 32, 33. A plurality of identical blades 26, are circumferentially spaced around the periphery of the disc 25. Although six blades are shown, any other number of blades suitable to the particular mixing operation could be used. The blades 26 are radially spaced from the hub 21. Each blade includes a flat, rectangular surface 27 which is symetrically disposed about the periphery of disc 25. The axial length or height of the blade, flat blade surface 27, is the same from both the upper and lower disc faces 32, 33. A pair of converging blade surfaces, 28, 29, extend respectively from the upper blade tip 38 and lower blade tip 39 to the middle of the next adjacent flat blade surface, 26A. The embodiment of the impeller 20 in FIGS. 3 and 5 further includes a pair of oppositely spaced curved inner and outer side walls 30, 31 which enclose the volume defined by the flat blade surface 27 and upper and lower surfaces 28, 29. In the embodiment shown in FIG. 4, the side walls 30, 31 are omitted.

EXAMPLES

A number of impellers having a variety of configurations were tested under standard conditions. These conditions included testing the impeller in a flat-bottom, vertical cylindrical tank having a diameter of 18 inches and a height of 18 inches. Four standard baffles were mounted equidistant about the inner wall of the tank. The impeller was positioned 6 inches off the bottom of the tank and was covered with 12 inches of water. Gas was introduced through a 6 inch diameter spargering centrally located in the tank, 5 inches from the bottom thereof. In each case, an impeller was fashioned from a 6 inch diameter disc to which six blades of various configurations were attached. For each blade configuration, readings were taken of the horsepower supplied to the impeller at a number of different angular speeds. From such data, the power number for a given impeller for both directions of rotation was calculated. By experimenting with a number of different configurations, it was learned that there appeared to be a relationship between the Np ratio and the degree of streamlining on one side of the blade while keeping the other side flat. On the basis of such experiments, it was determined that the maximum Np ratio could be achieved by an impeller which came close to maximizing the streamlining on one side of the blade and minimizing it on the other. Those results led to the development of the two embodiments shown respectively, in FIGS. 3 and 4.

For the configuration in FIG. 3, the radial length of the blades was 1½ inches, the axial length was 1¼ inches each, and the thickness was ⅛ of an inch. The configuration of FIG. 3 yielded an Np equal to 2.4 in the clockwise direction and equal to 1.4 in the counterclockwise direction. Hence, the Np ratio for the closed blade design was the lowest of all tested, 0.55. Stated another way, the impeller of FIG. 3 drew 55% less power where rotated in the counterclockwise direction.

Figure 4:
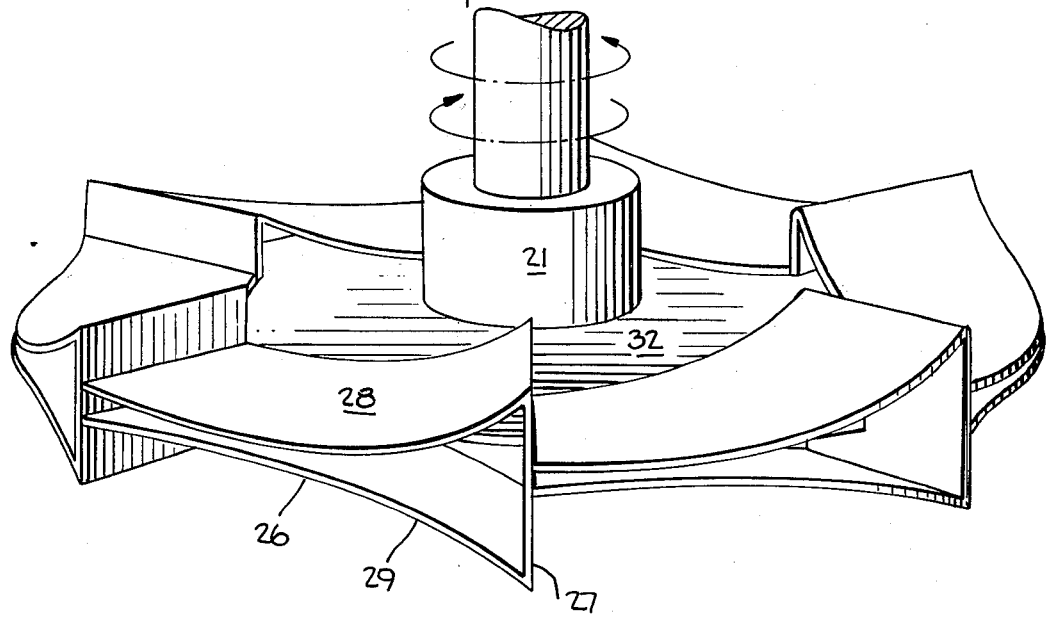
FIG. 4 is a perspective edge view of the invention with the blades open on their sides.

The impeller shown in FIG. 4 had similar dimensions; the only difference being that the blades were open on their sides. There, the power number in the clockwise direction was 4.2 and in the counterclockwise direction was 2.6, thus yielding a power number ratio of 0.64.

In another test, the mass transfer efficiency of the impeller 20 of FIG. 4 was compared with a similar size flat blade turbine. Mass transfer efficiency is generally defined as the quantity of gas absorbed by a liquid per unit horsepower. The test results indicated that at low power levels (10 HP per 1,000 gal. of liquid and lower) the impeller 20 operated at a higher mass transfer efficiency than did the flat blade turbine regardless of the direction of rotation. In other words, the impeller 20 has the capability of producing the same process results as the flat blade turbine but at a lower horsepower. Hence, at low power levels the impeller 20 saves energy due to its higher efficiency. Also, since either power number of the impeller 20 (4.2 or 2.6) is less than the power number (5.6) of the flat blade turbine, the impeller 20 operates at a higher speed (for a given input horsepower) thereby reducing the torque required for a given operation.

While the foregoing results were obtained with a relatively small scale impeller, those skilled in the art are able to fashion larger impellers, see, "Fermentation Mixing Scale-Up Techniques", J. Y. Oldshue, VIII Biotechnology and Bioengineering, pp. 3-24 (1966).

Thus, having described the invention as well as given details of its preferred embodiments, those skilled in the art will know that dual power number impellers can be fashioned by various alterations of the blade geometry without departing from the spirit and scope of the subject invention as expressed in the following claims.

I claim:

1. A process for agitating liquids having different viscosities by an impeller driven at substantially the same given speed for either direction of rotation comprising the steps of:
   (a) agitating a liquid of relatively light viscosity by rotating the impeller in a given direction at said given speed, the impeller having a plurality of blades substantially longer than they are wide disposed in end-to-end relationship about the periphery of a disc of the impeller, the blades having first longitudinal arcuate flow inducing surfaces for inducing flow primarily when the impeller is rotated in said given direction and second flat end flow inducing surfaces for inducing flow primarily when the impeller is rotated in the opposite direction,
   (b) introducing a substance into the liquid, whereby its viscosity is increased,
   (c) changing the direction of rotation of the impeller upon increase in the viscosity of the liquid to render the second flat end flow inducing surface primarily effective to induce flow rather than said first longitudinal arcuate flow inducing surface to reduce load on the impeller when rotated at said given speed in said opposite direction,
   (d) whereby load on the impeller is reduced at said increased viscosity of the liquid upon changing the direction of rotation of the impeller to prevent overload of the impeller, without requiring reduction in the speed of rotation of the impeller.

* * * * *